US008078479B2

(12) United States Patent
Greenman

(10) Patent No.: US 8,078,479 B2
(45) Date of Patent: Dec. 13, 2011

(54) METHODS AND SYSTEMS FOR PRESCRIBING SAMPLE PRESCRIPTIONS

(76) Inventor: Eric Greenman, Scottsdale, AZ (US)

( * ) Notice: Subject to any disclaimer, the term of this patent is extended or adjusted under 35 U.S.C. 154(b) by 833 days.

(21) Appl. No.: 11/908,397

(22) PCT Filed: Mar. 13, 2006

(86) PCT No.: PCT/US2006/009058
§ 371 (c)(1),
(2), (4) Date: Sep. 11, 2007

(87) PCT Pub. No.: WO2006/099384
PCT Pub. Date: Sep. 21, 2006

(65) Prior Publication Data
US 2008/0208626 A1 Aug. 28, 2008

Related U.S. Application Data

(60) Provisional application No. 60/660,780, filed on Mar. 11, 2005.

(51) Int. Cl.
G06Q 50/00 (2006.01)
(52) U.S. Cl. .................................. 705/2; 705/3
(58) Field of Classification Search .................... 705/2, 3
See application file for complete search history.

(56) References Cited

U.S. PATENT DOCUMENTS

| | | | |
|---|---|---|---|
| 5,628,530 A | 5/1997 | Thornton | |
| 5,797,515 A | 8/1998 | Liff et al. | |
| 5,832,449 A | 11/1998 | Cunningham | |
| 5,845,255 A * | 12/1998 | Mayaud | 705/3 |
| 5,845,264 A | 12/1998 | Nellhaus | |
| 6,021,392 A | 2/2000 | Lester et al. | |
| 6,055,507 A | 4/2000 | Cunningham | |
| 6,067,524 A | 5/2000 | Byerly et al. | |
| 6,098,892 A | 8/2000 | Peoples | |
| 6,152,364 A | 11/2000 | Schoonen et al. | |
| 6,155,485 A | 12/2000 | Coughlin et al. | |
| 6,170,746 B1 | 1/2001 | Brook et al. | |
| 6,202,923 B1 | 3/2001 | Boyer et al. | |

(Continued)

FOREIGN PATENT DOCUMENTS

WO 0028474 5/2000

(Continued)

OTHER PUBLICATIONS

Business/Health & Science Editors. "IMS HEALTH Strategic Technologies Launches SampleTrak". Business Wire. New York: Apr. 19, 2000. p. 1.*

(Continued)

Primary Examiner — Robert Morgan
Assistant Examiner — Robert Sorey
(74) Attorney, Agent, or Firm — Schmeiser, Olsen & Watts LLP

(57) ABSTRACT

Systems and methods are disclosed for providing sample prescriptions electronically and creating a complete data set of information regarding the life-cycle of the sample prescription. In one embodiment, a sample prescription system comprises a management module that stores files corresponding to sample prescriptions. Each corresponding file is linked to a unique sample code. The sample code and linked file together comprise an electronic history of the sample's life-cycle, which is built dynamically over time into a comprehensive code containing all information relevant to a prescribed sample and it's path to consumption.

8 Claims, 6 Drawing Sheets

U.S. PATENT DOCUMENTS

| | | |
|---|---|---|
| 6,260,761 B1 | 7/2001 | Peoples, Jr. |
| 6,561,977 B2 | 5/2003 | Williams et al. |
| 6,654,724 B1 | 11/2003 | Rubin et al. |
| 6,687,676 B1 | 2/2004 | Denny |
| 6,755,784 B2 | 6/2004 | Williams et al. |
| 6,859,780 B1 | 2/2005 | Cunningham |
| 6,877,658 B2 | 4/2005 | Raistrick et al. |
| 6,892,941 B2 | 5/2005 | Rosenblum |
| 7,058,584 B2 * | 6/2006 | Kosinski et al. ............... 705/2 |
| 2002/0013787 A1 * | 1/2002 | Pollard et al. ............... 707/507 |
| 2002/0032582 A1 * | 3/2002 | Feeney et al. ............... 705/2 |
| 2002/0161607 A1 | 10/2002 | Subich |
| 2003/0212577 A1 | 11/2003 | Nichtberger |
| 2003/0216831 A1 * | 11/2003 | Hart et al. ............... 700/235 |
| 2003/0216974 A1 | 11/2003 | Browne |
| 2004/0148195 A1 | 7/2004 | Kalies |
| 2004/0236607 A1 | 11/2004 | Kost et al. |
| 2004/0236630 A1 * | 11/2004 | Kost et al. ............... 705/14 |
| 2005/0010448 A1 | 1/2005 | Mattera |
| 2005/0033610 A1 | 2/2005 | Cunningham |
| 2005/0038673 A1 | 2/2005 | Stookey et al. |
| 2005/0060199 A1 | 3/2005 | Siegel |
| 2006/0224417 A1 * | 10/2006 | Werner ............... 705/2 |

FOREIGN PATENT DOCUMENTS

| | | | |
|---|---|---|---|
| WO | 0115006 | | 3/2001 |
| WO | 2006099384 | * | 9/2006 |

OTHER PUBLICATIONS

Business Editors/High-Tech Writers. "Synergistix Introduces C.A.T.S. Tablet PC Edition", Business Wire. New York: Mar. 7, 2003. p. 1.*

* cited by examiner

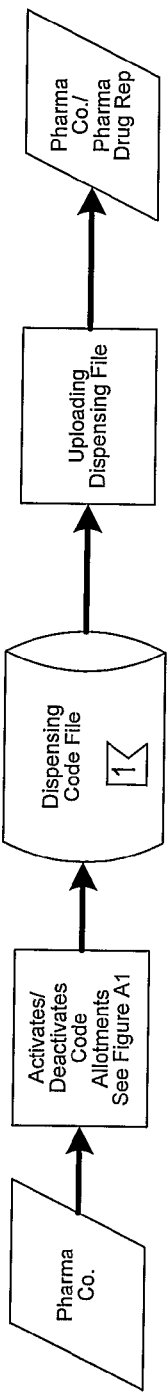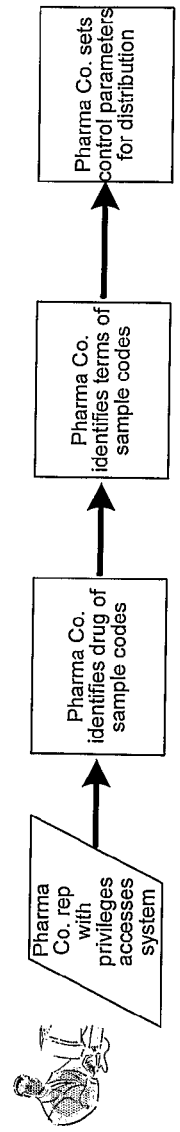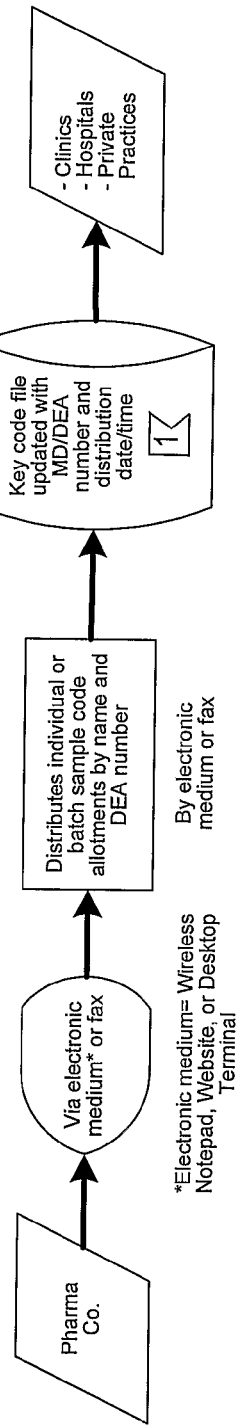
Fig. 4A-B

UNIVERSAL SAMPLE PHARMACY CODES (USPCs)
Figure C. Sample Code Prescription Through Physician/Prescriber (Via Electronic Medium)
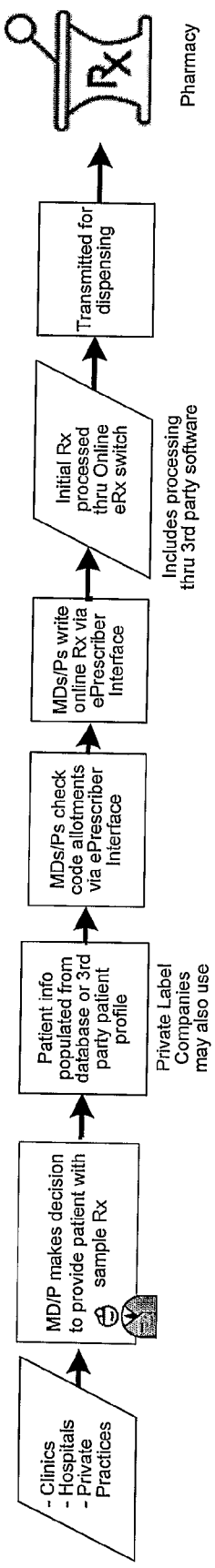
Figure D. Sample Code Prescription Through Physician/Prescriber (Via Fax or Manual Process)
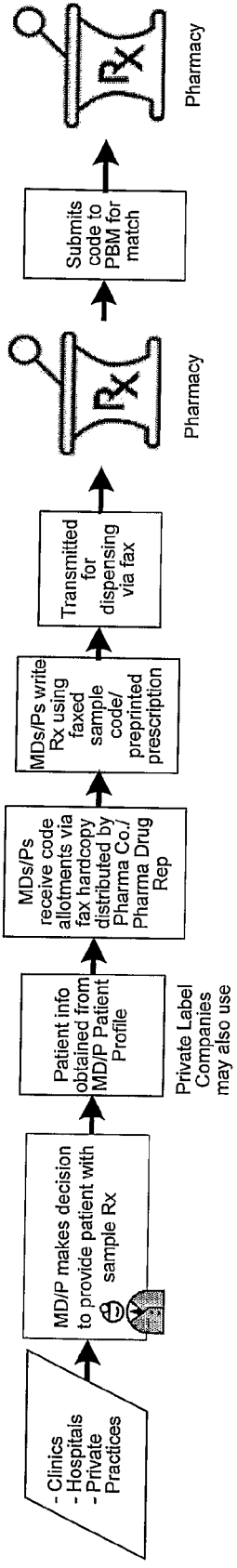
Fig. 4C-D
Legend:
MD/P = Medical Doctor/Prescriber

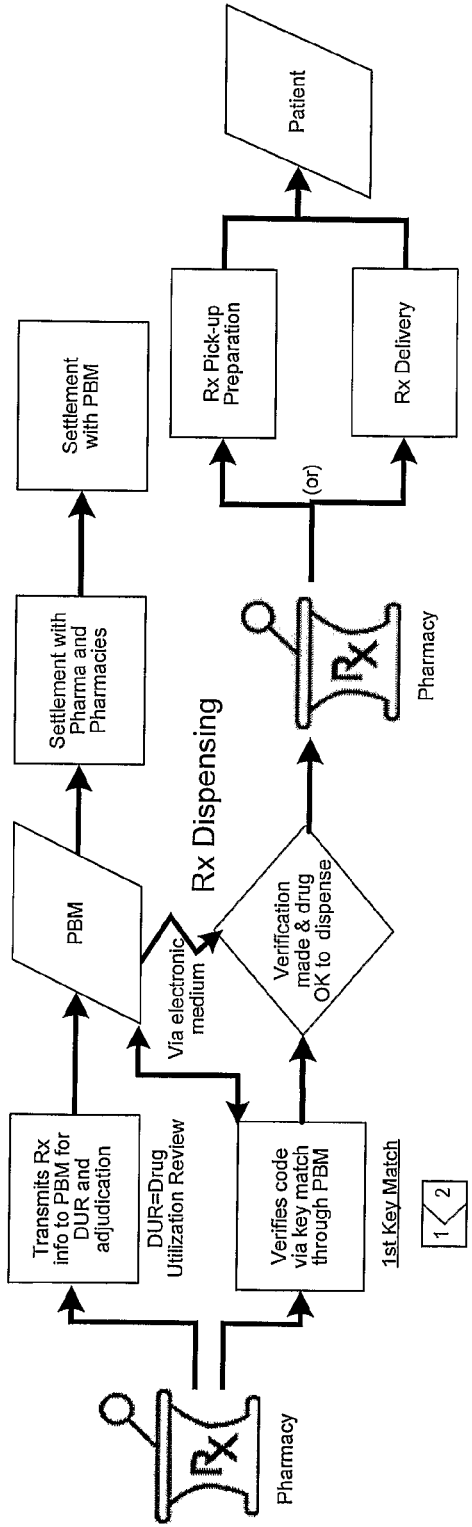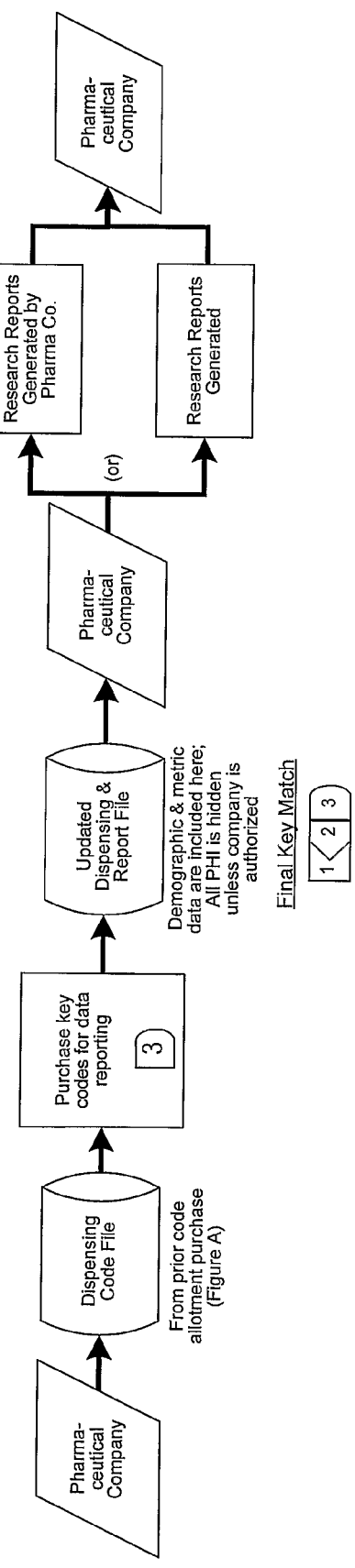
Figure E. Patient Receiving Sample
Figure F. Pharma Purchase of Demographic & Metric Data
Fig. 4E-F

METHODS AND SYSTEMS FOR PRESCRIBING SAMPLE PRESCRIPTIONS

BACKGROUND

To market their products, pharmaceutical companies commonly provide samples of the products to physicians, such as sample prescription medications. Typically, a pharmaceutical representative visits a physician's office where the representative discusses with the physician such things as the applications of their product and advantages of their product over competing products. The representative may then provide the physician with free samples of the product (packaged as, for example, blister packs, bottles or sample boxes) to prescribe to patients. This serves two principle purposes. First, it is hoped the patients will like the samples and will want to continue use of the product. Second, it is hoped that the physician will learn from the patients using the samples that the product is effective, causing the physician to prescribe or recommend the product to future patients. There are also other reasons pharmaceutical companies give out samples. For example, pharmaceutical company sponsored patient assistance programs provide both samples and regular prescriptions of medications to those unable to afford the medications.

However, the current process of distributing and prescribing sample prescriptions suffers from numerous problems. First, there is insufficient control over who receives the samples. It is intended that the physicians or pharmaceutical companies give the samples to deserving patients. However, the current system has inadequate control checks, occasionally resulting in samples being misused by patients (e.g. used abusively) or redirected to unintended users. Second, the current system typically has insufficient examination procedures to determine whether or not a sample prescription is right for a particular patient. For example, the patient may be taking a different drug that adversely interacts with a sample medication. Third, the companies providing the products (e.g., pharmaceutical companies) desire better sample prescription tracking information for marketing purposes. Current prescription tracking systems only provide limited information, which is typically inadequate for comprehensive marketing evaluations. Other attributes of the current system are also inefficient for the provision of products from the physician's perspective, including the need for additional paperwork related to ordering or receiving physical stock of the products. This may be in the form of shipping companies requiring signatures to validate receipt of products, which demand more time throughout the process from the physician. The involvement of pharmaceutical company representatives also creates inefficiencies from the regular turnover of personnel, which may result in depleted sample stocks not being replenished in a timely fashion. This disrupts patient care for the physician. Fourth, the current sample prescription system frequently results in waste. For example, pharmaceutical companies frequently provide sample prescriptions to physicians in packaged sample containers that have expiration dates. The packaging itself is expensive, and further waste is added if the samples are not given to patients prior to a sample's expiration date. Disposal of expired samples poses a health risk to the general public in that samples may end up either in dumpsters or flushed into the water system. This has resulted in significant levels of medication found in lakes and municipal water systems. Fifth, after new U.S. Food and Drug Administration ("U.S. FDA") Black Box Labeling regulations were implemented, all antidepressant packaging inserts inside sample boxes needed to be recalled and replaced with U.S. FDA compliant samples having updated inserts. This resulted in expensive shipping and repackaging costs. Sixth, as a further result of new U.S. FDA Black Box warnings and labeling, pharmaceutical companies have been initiating new policies resulting in discontinuing distribution of many types of samples (e.g., certain classes of medication) to pediatric practices. Consequently, the pharmaceutical companies are requiring the physicians to sign "reinstatement requests" in which the physician certifies that they examine and treat adult patients that require that class of medication. Otherwise, the pharmaceutical company will not provide the samples to the physician. This is an often lengthy process requiring the completion of many forms that may not be readily accessible. This causes delay and additional work for the physician in obtaining samples, which may disrupt patient care. Moreover, there has been no mechanism in place to streamline this authorization process.

The overriding impetus for pharmaceutical companies to move away from traditional sampling is that the cost of packaging, warehousing and distributing the samples, under current practices, is very expensive. This ultimately raises the cost of medications from production all the way down to what the patient eventually pays for their prescriptions. One fashion in which pharmaceutical companies have attempted to address this is by introducing different media, which can be distributed to patients by physicians and taken to a dispensing pharmacy to collect the sample. Current media in the marketplace include paper vouchers and magnetic strip cards, among other things (all of which have expiration dates which leave gaps in initiating new prescriptions written, and require additional storage space in the prescribers' offices). These approaches remove the physician from needing to maintain sample box inventory at their office, but create an inconvenience in the process by requiring the transfer of the media between the participants in the sample chain. While it does create a partial electronic record of the dispensing of the sample to the patient, many significant data gaps in the sample's life-cycle remain.

Some attempts have been made to remedy some of the above-described problems. For example, some are attempting to implement radio frequency identification ("RFID") systems. However, such RFID systems have many disadvantages, including, among other things, being unreliable. Other gaps in the RFID systems as applied to pharmaceutical company samples include a maximum radius for tracking, high expense in tracking to the individual package (beyond a bulk shipment), and the absence of recipient information (e.g. gender, age, diagnosis code, etc.) that is critical in the distribution of a healthcare product such as a prescription drug sample.

For the foregoing reasons, there is a need for improved systems and methods for giving sample prescriptions.

SUMMARY

The preferred, non-limiting embodiments of the present invention are directed to systems and methods that satisfy the need for providing sample prescriptions electronically (thereby bypassing the need for packaging and shipping sample medications) and creating a complete data set of information regarding the life-cycle of the sample prescription. A sample prescription system having features of the present invention comprises a management module that stores files corresponding to sample prescriptions. Each corresponding file is linked to a unique sample code. The sample code and linked file together comprise an electronic history of the sample's life-cycle, which is built dynamically over time into a comprehensive code containing all information relevant to a prescribed sample and it's path to consumption. The sample codes are allocated to subscribing pharmaceutical companies, who in turn distribute the sample codes to physicians. Prior to the allocation of the codes the code itself is an "empty set" devoid of any data except a unique coded identifier, or Universal Tracking Pharmacy Code ('UTPC'). The unique UTPC is the coded string that identifies the life-cycle of the prescription or sample to which it is assigned, once it is distributed by an authorized physician. As a matter of form, the present invention provides for an infinite number of UTPCs to be available to allocate to physicians. UTPCs may ultimately be attached to several fields or character strings that are commonly used in prescription tracking for which there are already recognized standards (e.g. prescription number, national drug code, etc.). Inherent in this process is the ability to control the distribution of codes for the class/type of medication they represent and the physicians that are chosen to have access to samples of that drug. This automatically reduces exposure to pharmaceutical companies since physical samples or sample media are not physically present in the environment to be misdirected to non-approved physicians/specialties or patient groups for which the medication is not U.S. FDA approved. The physicians use the codes to assign specific samples to patients by transmitting the sample code, along with a prescription, to a dispensing entity, such as a pharmacy, for delivery to the patient.

Throughout the above-described process, information about the sample prescription is acquired by a management module and appended to a file corresponding to the sample code. Such information may generally include information about the prescribing physician, the dispensing pharmacy and the patient using the sample prescription. Dates and times of actions connected to the samples may also be captured.

The entire electronic process together creates a uniform utility for tracking sample information throughout it's life-cycle from allocating the sample code to the physician, to the physician assigning the sample code to a drug and patient, to the recipient patient obtaining the prescription from an appropriate dispensing entity.

Several parties may derive benefit from the uniform utility that captures this information such as a pharmaceutical company, governmental or regulatory agency, or the physician or physician group through which the sample codes were originally provided. They may have access to portions of the aggregate information stored in the files, which may advantageously be used for marketing purposes.

A first aspect of the present invention includes the creation of a permanent relationship between two distinct data sets, which include a static pharmacy tracking code known as a Universal Tracking Pharmacy Code and a linked file that dynamically builds as information is added. A first half of the tracking code is possessed within a pool with alpha-numeric sequences that may be put into building a bar code that may be used by pharmacies and pharmaceutical companies. A management entity owns the tracking codes and corresponding files (which together comprise a unique code) for their use and sale and manages all access to the codes and files. The management entity builds and administers these codes. Hospitals, clinics, pharmacies, insurance companies, governmental agencies and the like may reference these codes to obtain tracking information. Use of a code itself is tracked, so that any time it is used the sample prescription system tracks its use by connection to partner companies through which the codes pass for routing instructions (an example of this is a pharmacy claim 'switch' company, such as NDC Health or Emdeon). As data is collected, it is appended to files corresponding to the assigned code. The management entity may then disseminate selected tracking information to subscribing entities for a user fee.

A second aspect of the present invention is an aggregate code which is born of the related data sets created by the first aspect of the invention. This aggregate code is referred to as a "Universal Sample Pharmacy Code" (or "USPC"). A USPC is a UTPC that pharmaceutical companies purchase to use for direct attachment to distribution of samples or prescriptions, then receive data to track the life cycle of that sample or prescription. The USPC is a UTPC which has been attached to a file that is populated with information captured from numerous sources throughout the life-cycle of the sample or prescription. As described above, the USPC is comprised of a UTPC and an electronic file which includes all available history of that code. The USPC may be embodied in an encrypted character string of a 128-bit or 256-bit key. As the life-cycle content is built into the file attached to the UTPC, it is then encrypted into the character string so that a user with the encryption key may access the current data. A physician writing a prescription may pull from a preset pool of sample codes allocated by a pharmaceutical company. The pharmaceutical company may also select the number of sample codes they wish to allocate (e.g., 50,000, 100,000, or over a million codes). The pharmaceutical company may choose to allocate and terminate their initial sample codes via a secure electronic interface by authorized representatives of the pharmaceutical company.

In a third aspect of the present invention, the aggregate code, including both the UTPC code and the USPC, are encrypted into a data packet and may additionally have bundled with them software/next directions and a self-executing program for each pharmacy to universally open up an information window enabling the pharmacy to read information contained in the codes. The software may additionally comprise import/integrate software that provides for seamless integration of code information in a pharmacy's computer system. This integration may allow a pharmacy system to directly feed the sample code information into their transmission for adjudication. Access to read the data carried in the code for manual entry to initiate adjudication shall also be supported in the software. When implemented, and after the sample prescription is either given to the patient, picked up, mailed, or otherwise delivered to the patient, the code may support creation of a bar code to be used for scanning by a conventional scanner. This may bundle the code into an encrypted state within the data packet that is now represented by a bar code. It may then be sent to a sample prescription manager as instructed in the software attached to any scanning system able to read the bar code.

In a fourth aspect of the present invention, the users contract with the management entity for the sample prescription services. The contracted user is provided with a unique "unbundler" code (also referred to as a "key") enabling the user to view the sample prescription information contained in the aggregate code. If the code has been encrypted, the key would allow for the activation of the software that functions to decode the character string that represents the UTPC and attached files (the USPC). The contracting users (e.g., pharmaceutical companies) pay for use of the sample prescription services via electronic deposit automatically as invoiced electronically, given the high number of codes used.

In a fifth aspect of the present invention, a first part of the USPC may contain the following information and is present in the USPC after the pharmaceutical company allocates the code to the physician:

A) 11-digit National Drug Code ("NDC-11" which includes the drug manufacturer, dosage and form, and package type)
B) Quantity available
C) Terms of patient contribution (e.g. free sample, dollars-off, number of refills available)
D) Version of medication (e.g., in capsule, tablet or liquid form)
E) Bin number
F) Group number, and other processing variables to support adjudication
G) Unique physician number or NPI ("National Provider Identification") number In a sixth aspect of the present invention, other parts of the USPC are added at various steps after the corresponding prescription is written and dispensed and new information is communicated back to the USPC Management Module. These parts of the USPC may contain the following information:

Date prescription written
Sig (directions)
Diagnosis code
Zip code of origin/dispense zip code
Hospital/clinic of origin code (inpatient vs. outpatient)
Patient Social Security number, date of birth, age, sex
Payer coding
Date prescription filled and received by patient
Dispensing pharmacy data In a seventh aspect of the present invention, the first half of the USPC as noted above is in a pool of sample codes that a physician may pull from to write prescriptions. These codes are created, distributed, attached to active prescriptions, and transmitted to the dispensing pharmacy electronically. This replaces the pharmaceutical company's need to produce wasteful sample boxes of medications. Instead, the codes are purchased by pharmaceutical companies for less than what it costs them to produce samples of their medications (effectively an electronic trial sample code). The codes are then housed in a central location for national distribution by local pharmaceutical representatives or other centrally located authorized representatives. The actual product is then provided to the receiving patient from the regular operating inventory of the dispensing pharmacy upon request from the authorized patient.

After the aggregate USPC code is built with collected data following a prescription being dispensed to a patient (e.g., a first part of the code plus other parts of the code), then contracting users, such as pharmaceutical companies, may purchase select information that has been built into the USPC. Preferably, the contracting user is only granted access to confidential information as dictated by current laws such as, in the United States, the Health Insurance Portability Accountability Act ("HIPAA"). For example, information that may be restricted from contracting subscribers includes a patient's social security number and other personal, confidential information. The other non-confidential demographic information may be used by pharmaceutical companies, as an example, for tracking all sample prescriptions. If a USPC arrived at the filling pharmacy and was designated in the first part of the code as a free sample, then it would allow for the sample prescription to be filled for no cost to the patient. Other structures of an offer such as a dollar-amount off the prescription may be administered through the code. The dispensing pharmacy will be reimbursed by the pharmaceutical company for the cost of filling the sample prescription via the functions of a pharmacy benefit manager ("PBM"). The PBM would verify the code carries the financial terms (e.g. number of units, free, dollar-amount off) intended by performing an eligibility function on the code submitted from the dispensing pharmacy. The PBM also becomes a central vehicle for capturing dispensing and patient data for relay back to the Management Module which builds on the code and the corresponding data files, which ultimately complete the entire USPC aggregate code. Desirably, the cost for distributing promotional products in this fashion is less than what a pharmaceutical company pays for fulfillment and distribution of samples using current methods.

Although the aggregate USPCs, when completed, would be available, the pharmaceutical companies would not have to buy the accompanying data if they choose not to. All of the USPCs (UTPCs and corresponding data files) are encrypted, and pharmaceutical companies are only able to get the tracking information if they purchase a final key which grants them access to the USPC (UTPC and corresponding data files).

In an eighth aspect of the present invention, in order to overcome barriers that organizations may have regarding these codes and development/implementation on their system, "turnkey" software is provided so that little or no programming is required on behalf of any users of the sample prescription system. This enables the users to interface and integrate with software already installed on the users' organization's system(s).

A ninth aspect of the present invention is that the management entity stores prescription information in a central database, protected by security measures to ensure that confidential information is not unlawfully obtained.

A tenth aspect of the present invention is centralizing and standardizing prescription sampling and tracking. In this manner the present invention serves as a neutral clearinghouse and utility service for manufacturers that provide samples as promotional products.

For purposes of summarizing the invention, certain features, aspects and advantages of the invention have been described herein above. It is to be understood, however, that not necessarily all such features, and aspects are used, and advantages achieved, in accordance with any particular embodiment of the invention. Thus, the invention may be embodied or carried out in a manner that achieves or optimizes one feature, aspect or advantage as taught herein without necessarily achieving other advantages or using other aspects as may be taught or suggested herein.

DRAWINGS

These and other features, aspects, and advantages of the present invention will become better understood with regard to the following description and accompanying drawings where:

FIG. 4 A-F is a flow diagram of a further embodiment of the sample prescription system process in accordance with the present invention.

DESCRIPTION OF PREFERRED EMBODIMENTS

A. System Architecture

Figure 1:
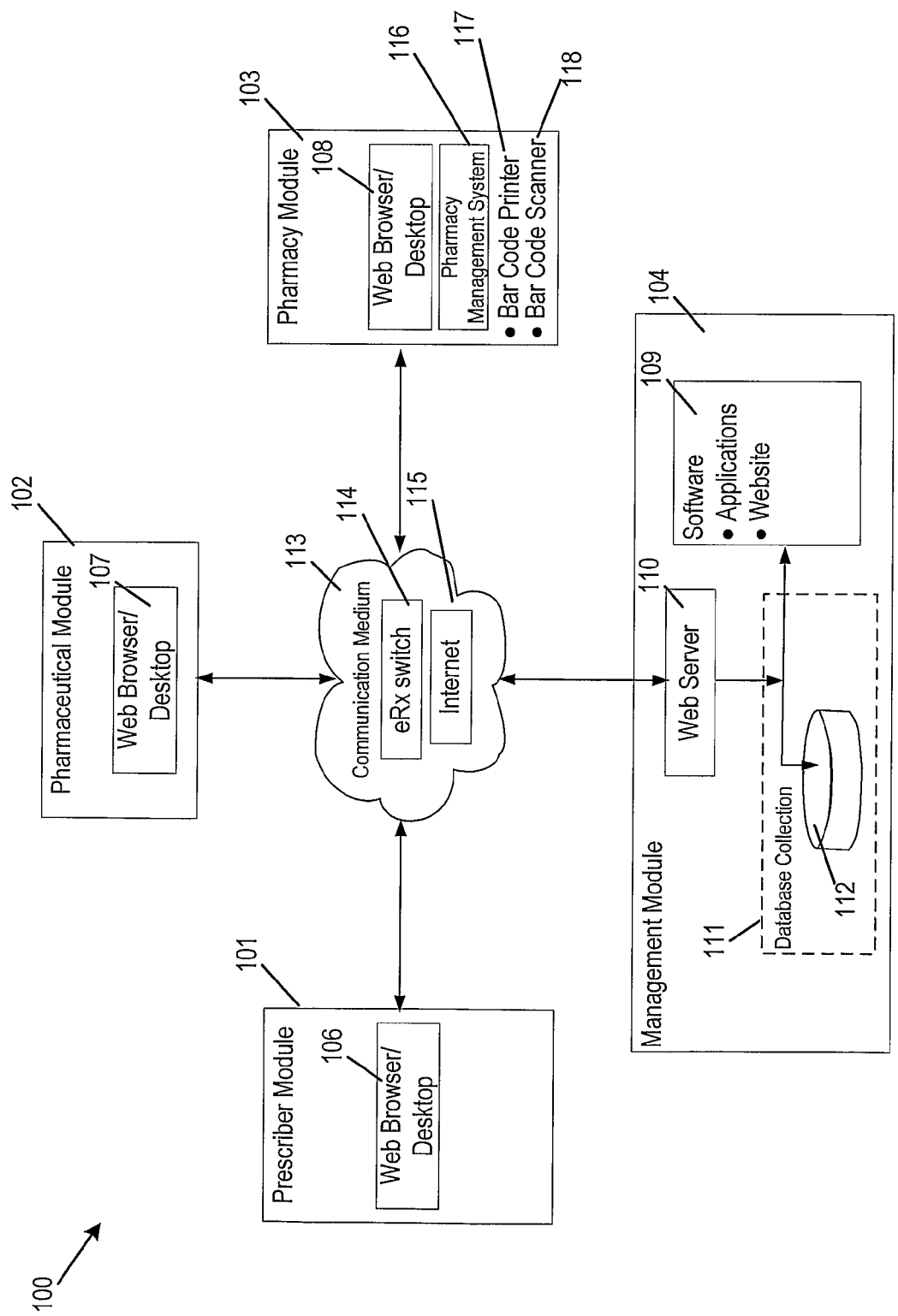
FIG. 1 is a diagrammatic illustration of the general architecture of one embodiment of a sample prescription system of the present invention.

FIG. 1 illustrates one non-limiting embodiment of the general architecture of a sample prescription system 100 (herein also referred to as "SPS") that operates in accordance with the present invention. The SPS 100 includes a prescriber module 101, a pharmaceutical module 102, a pharmacy module 103 and a management module 104, that communicate via communication mediums 113, such as an electronic prescribing switch 114, and the Internet 115.

1. Prescriber Module 101

The prescribing module 101 may be implemented using any type of computing device for operating a web browser 106. The computing device is defined as a device that enables a user to browse a remote web site through the communication medium using, for example, a web browser, such as Microsoft® Internet Explorer developed by Microsoft Corporation. Examples of the computing device include a desktop computer, a lap top computer, a personal digital assistant, an interactive wireless communications device, a handheld computer, a computer server, or the like, which connects with the communication medium. Additionally, the computing device may include any number of known peripheral devices that cooperate with the computing device, such as a printer, a scanner, a bar code scanner, facsimile machine and the like.

The prescriber module 101 is located where sample prescriptions are prescribed, such as a medical private practice, a hospital, or a clinic. In general, the prescriber module 101 enables a prescribing entity, such as a physician, to access the management module 104 to distribute sample prescription codes and prescribe a sample to a patient via an electronic prescription switch. The distribution of a code to a patient is paired with the electronic prescription when completed in the prescriber module 101 and sent into the communication mediums 113. The paired data may then be split into two transmissions at the management module 104, with the electronic prescription being submitted to the electronic prescription switch (denoted as eRx switch) 114 for ultimate delivery to the chosen pharmacy. A switch refers to an organization that receives live pharmacy claims from a pharmacy management system and then routes them to the appropriate claims processor for PBM functions. Once the claims processor adjudicates the claim and sends a response, the switch also returns the adjudicated claim from the claims processor to the management module 104 from where it originated. The USPC is updated with the new information received at the management module 104 during this step and is then stored to be made available to other users with appropriate access.

2. Pharmaceutical Module 102

The pharmaceutical module 102 is implemented using one or more computing devices for operating a web browser 107. The pharmaceutical module 102 may be located at a company's physical facilities. It is also contemplated that the pharmaceutical module 102 comprises a main server located at a pharmaceutical company's facilities, which may be remotely accessed by other computer devices. For example, pharmaceutical sales representatives may access the pharmaceutical company's server via a wireless personal digital assistant device, which advantageously enables the sales representatives to access the management module 104 remotely. Alternatively, the wireless personal digital assistant device may be capable of accessing the management module 104 directly without having to first access the pharmaceutical company's server.

The pharmaceutical module 102 contains within it various levels of permission to assign drugs, patient terms, and physicians to sample codes. Specifically, it is contemplated that an appropriate party at the pharmaceutical company has protected administrative entry screens to control the drug chosen for available sample codes and how many are available to a given employee and physician. The party also controls the patient terms (e.g. free or patient contribution, number of refills, etc.) and establishes parameters for the code distribution such as a maximum number of codes for a specific product to a specific physician, and may also designate the maximum number of authorizations allowed per patient.

3. Pharmacy Module 103

The pharmacy module 103 is also implemented using one or more computing devices for operating a web browser 108. The pharmacy module 103 is at a location that dispenses prescriptions and sample prescriptions. The pharmacy module 103 is capable of accessing the management module 104 and receiving information sent from the management module 104, such as emails, via the communication medium 113. The pharmacy module may also be used to apply a key to the sample code in the management module and access the stored data for that sample code. The pharmacy module 103 may also contain an application to receive electronic prescriptions from the electronic prescription switch 114 in addition to the tools to access the management module 104.

4. Management Module 104

In general, the management module 104 provides functionality for managing sample prescriptions utilized in the SPS 100. Typically, the management module 104 is operated by a business entity that handles various sample prescription order processing tasks, collections, distribution of information and customer service tasks associated with the SPS 100. The management module 104 may include software 109 that implements an online registration process (not shown) for enabling other entities, such as physicians, physician practice groups, hospitals, clinics, pharmaceutical companies, pharmacies, and so forth, to register as members. The management module 104 contains administrative screens which allow various users with the appropriate privileges to establish terms to apply to the codes, as referenced above under Section 2, 'Pharmaceutical Module 102.' The management module 104 may identify customers using any appropriate method, such as cookie retrieval or log-in procedures. Additionally, communications between devices of the SPS 100 preferably use an authenticated certificate in accordance with governmental regulations, such as U.S. Drug Enforcement Administration ("DEA") policy.

The management module 104 illustrated in FIG. 1 includes components that may be used to implement the above-described features. The exemplary management module 104 includes a web server 110, which accesses a database collection 111 that includes a database of sample prescription information 112 and related content. The web server 110 also manages a web site accessible via the communication medium 113. The web server 110 may also process requests made with an appropriate permission level or de-coding key for the sample prescription information contained in the aggregate code and the attached files, review and authenticate the sample prescription information, and send and receive sample prescription information to and from the prescriber module 101, the pharmaceutical module 102 and the pharmacy module 103 via the communication medium 113. The information may be used to provide sample prescriptions to patients via submission to the electronic prescribing switch 114, track the sample prescriptions and generate sample prescription marketing reports among other functions.

The web server 110 communicates with management module software 109 as well as the database collection 112 to manage the sample prescription process and to provide prescription related information to appropriate users. Additionally, the management module software 109 generally implements the functions of the management module 104, including releasing information, populating the database 111 and operating the management module web site.

a. Database Collection 111

The database collection 111 illustrated in FIG. 1 includes the database 112 for storing sample prescription related information. The database 112 contains a plurality of files, each designated by a unique encrypted alphanumeric sample code corresponding to a sample prescription. In other words, each sample prescription used in the SPS 100 has a corresponding file in the database 112 that, together with the tracking code, represent the aggregate sample code that is the USPC. The sample code may be randomly generated or may be generated using a convention where the sample code has specific meaning. Specifically, in the latter instance, a person with knowledge on how to read the sample code may obtain information about the corresponding sample prescription by analyzing the sample code. For example, the sample code may have a first portion that identifies the pharmacy company of origin, a second part that identifies the type of drug corresponding to the prescription, and the like.

The files in the database 112 contain fields that are capable of being populated with desired prescription information as the corresponding sample prescription moves through the SPS 100 process and data from different users is returned to the management module 104. In general, the fields contain information that a pharmaceutical company using the SPS 100 would find useful and information that will aid in the sample prescription distribution process. Examples of such fields include:

NDC-11 code for the drug
Sample prescription quantity available
Terms of patient contribution (e.g. free sample, dollars-off, number of refills available)
Date prescription written
Sig (i.e. directions how the medication is to be administered to the patient)
Diagnosis code (in format of ICD9 & ICD10 nomenclature)
Unique physician number, NPI number or DEA number
Zip code of origin or sample prescription dispensing location zip code
Hospital or clinic of origin code (e.g., inpatient or outpatient)
Patient information, including social security number, date of birth or age, and sex. (Advantageously, the patient's information may be used by the government authorities to prevent or apprehend "physician shoppers," and flag or alert the prescription filling pharmacy that the patient recently had a similar prescription filled.)
Payer coding
Date sample prescription filled and other dispensing pharmacy data related to this transaction
Sample code activation or deactivation date
Version of medication (e.g., type of tablet, capsule or liquid)
Prescription BIN number
Drug representative unique identifier for pharmaceutical company reference In an exemplary embodiment, the fields are populated by inputting information into the SPS 100 by the prescriber module 101, the pharmaceutical module 102, the pharmacy module 103 or from another source, such as a pharmacy benefit manager or electronic prescription switch, that has the desired information. The information may be inputted in any number of ways known by those skilled in the art, such as automatic uploading when a triggering event occurs during the SPS process or manual inputting of the information.

In connection with the database collection 111, in one embodiment, there may be several processes (not shown) such as ID generators, number generators and temporary storage units that may work with the database collection. Furthermore, it is recognized that the database collection 111 may be implemented using a variety of different databases such as relational databases, flat file databases, or object oriented databases. Moreover, while the database collection depicted in FIG. 1 is comprised of one database 112, it is recognized that in other embodiments, the database collection may include other databases. In addition, the database collection may be implemented as a single database with separate tables or as other data structures that are well known in the art such as linked lists, stacks, binary trees, and so forth.

5. Communication Mediums 113

The communication mediums 113 include an electronic prescription switch 114 and the Internet 115, though a wide range of interactive communication mediums may be employed in the SPS 100 as is well known to those skilled in the art via encrypted, HIPAA compliant encoding.

6. Other Embodiments

While FIG. 1 illustrates an embodiment wherein the management module 104 primarily implements the SPS process, it is recognized that in other embodiments, the management module 104 may include or work in conjunction with one or more third parties (not shown) to provide the sample prescription service. In some embodiments, the third party web site may receive requests for samples and/or send sample prescriptions to the pharmacies. In other embodiments, a pharmacy benefit manager may be central to communicating data between the management module and the users that interact with the sample code along the chain to a patient receiving a sample.

Furthermore, although the embodiments described herein use web site technology to disseminate information, a variety of electronic dissemination technologies may be used.

In addition, although the SPS 100 is described using "a" management module 104, it is recognized that the management module 104 may comprise multiple different sites.

B. Sample Prescription Process Using the Sample Prescription System 100

Figure 2:
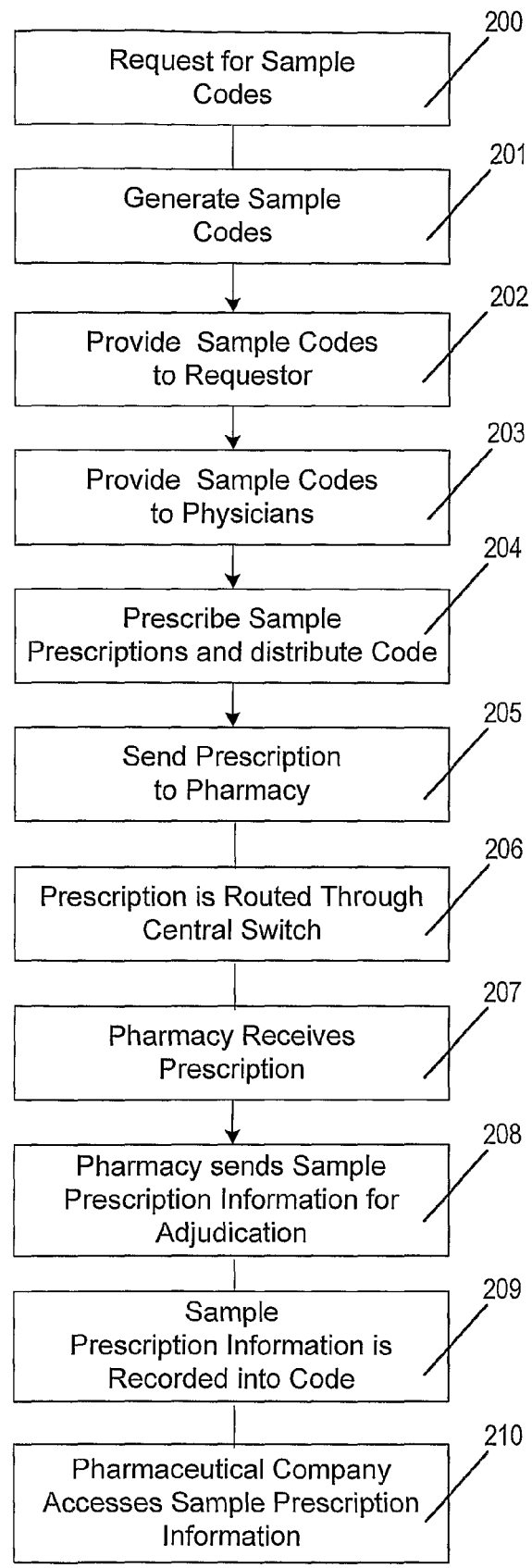
FIG. 2 is a flow diagram of one embodiment of the sample prescription system process in accordance with the present invention.

A description of the sample prescription system process using the sample prescription system 100 is described with particular reference to FIG. 2. In a step 200, a pharmaceutical company, via the pharmaceutical module 102, requests an allotment of sample codes from the management module 104. In an exemplary embodiment, the pharmaceutical company uses the pharmaceutical module 102 via web browser 107 to accesses the web site of the management module 104. Once logged into the web site, the web site provides an option for the pharmaceutical company to request an allotment of sample codes. Additionally, the web site prompts the pharmaceutical company to submit information about the sample prescriptions that will be used in conjunction with the sample codes. This information may include the number of requested sample codes, the corresponding sample prescription medication type, the terms available for the patient with that sample code, length of time the pharmaceutical company desires sample codes to be valid and any other pertinent information available at this time.

In a step 201, the management module 104 generates a number of sample codes corresponding to the number of sample codes requested in the step 200. An alternate mode of generating codes is a virtual "infinite" number of codes for the pharmaceutical company to activate sequentially. The management module 104 also creates a file corresponding to each sample code, which is stored in the database 112. Thus, each sample code corresponds to one sample prescription that the pharmaceutical company plans to distribute. Furthermore, information obtained during the step 200 is populated into the corresponding sample code file to build the aggregate sample code, or USPC.

In a step 202, the management module 104 provides the sample codes to the requesting pharmaceutical company. In an exemplary embodiment, the management module 104 emails a list of sample codes that correspond to the files created in the step 201. Alternatively, the pharmaceutical module 102 may be capable of downloading the list of sample codes or otherwise accessing the list of sample codes via the management module web site. Of course, other methods of transmitting the sample codes may also be used, such as via regular mail or faxing.

In a step 203, the pharmaceutical company activates allotments of the sample codes and provides them to prescribing physicians, which may be accomplished in any number of ways. For example, a pharmaceutical company sales representative may visit the physician's office and discuss the sample prescriptions with the physician. The sales representative may then use a wireless personal digital assistant to access the list of available sample codes corresponding to the desired sample prescription parameters and transmit (e.g., via email, fax or other electronic means) a number of sample codes to the physician for the physician's use. The sample codes may be transmitted with prepared hard copy prescriptions (e.g., paper form) having the physician's demographic data for simplifying the prescription process. Alternatively, the sales representative may provide the sample codes to the physician by "reserving" a number of sample codes. The physician may thereafter access the reserved sample codes via the management module web site.

In a step 204, sample prescriptions are prescribed to a patient. Here a patient visits a physician whom was previously allocated sample codes as discussed above. Alternatively, the patient-physician examination may be performed via a real time video conferenced appointment. The physician examines the patient and determines that the patient should take a particular medication. The physician then accesses the list of sample medications allocated to him by, for example, accessing the management module web site or a third party e-prescribing entity's web site.

There are a number of alternative ways in which the physician can prescribe the sample prescription. In one embodiment, the physician accesses the management module web site or third party e-prescribing entity if the prescriber module 101 includes access to both. The physician then navigates to an application of the web site that enables the physician to "e-prescribe" the sample prescription. In general, "e-prescribe" means that the physician can use a computer device to transmit the prescription to a medication dispensing facility, such as a pharmacy.

The "e-prescribe" application prompts the physician for information required to fill the prescription. This information may include the desired dispensing location (e.g. pharmacy location), patient information (e.g. name, age, sex, and other identifiers) and sample code, if any. If a sample code is provided, then the prescription is for a sample prescription corresponding to the sample code. The sample code may be verified by submission to a pharmacy benefit manager as the prescription number or the patient ID field. The physician then submits the prescription, and the information is routed to the management module 104. The management module 104 may then perform any number of processes, including populating the fields of the file corresponding to the sample code in the database 112 and checking the database collection 111 to determine whether or not the patient was recently prescribed similar medication that may indicate unlawful conduct (e.g. "physician shopping"). The SPS 100 also may authenticate the prescriber by verifying that the prescriber is lawfully able to prescribe the medication by referencing the prescriber's DEA designation.

In a step 205, the prescription is sent to a participating dispensing location. In an exemplary embodiment, the "e-prescribe" application transmits the prescription from the management module 104 to the pharmacy module 103 via the communication mediums 113. The communication mediums may or may not include a combination of the electronic prescription switch 114 and the Internet 115. In alternative embodiments, the prescription may be sent via fax. For example, a hardcopy of the sample prescription, which was provided by pharmaceutical representative, may be used.

In a step, 206, before reaching the pharmacy module 103, the prescription is routed to an organization that administers the electronic prescription switch 114, such as SureScripts, located in Alexandria, Virginia, and having a web site at the web address: www.surescripts.com, or RxHub, LLC, located in St. Paul, Minn., and having a web site at the web address: www.rxhub.net. The transmission to the electronic prescription switch 114 may be initiated by an e-prescribing application with direct access to the switch 114 or through the management module via the Internet 115.

In a step 207, the pharmacy module 103 receives the sample code and electronic prescription, triggering any number of actions. If the electronic prescribing switch 114 has accessed the appropriate PBM prior to delivery of the sample code and prescription to the pharmacy module 103, than the pharmacy may dispense the sample and complete a dispensing confirmation to send to the PBM. If the PBM has not yet been accessed, the pharmacy module 103 instructs a pharmacy's practice management system, which may or may not be part of the pharmacy module 103, to send the prescription to the appropriate PBM for adjudication. In general, in the step 208, the SPS 100 preferably coordinates with a pharmacy benefit manager verification that the sample prescription is valid (e.g. not forged), authenticates that the prescription originated from the management module 104 and determines whether or not the sample prescription is likely to cause an adverse reaction with other medications taken by the patient. In one embodiment, the pharmacy module 103 receives the prescription in the form of an encrypted email or faxed sample prescription having a bar code.

In a step, 209, the pharmacy module 103 transmits sample prescription information to the management module 104 via the PBM. In a preferred embodiment, the pharmacy module 103 may automatically transmit the desired information when the sample prescription is delivered to the patient as an additional transmission. For example, the pharmacy module 103 may produce a bar code (e.g., print a bar code label via a printer 117) that is affixed to a package (e.g., container) of the sample prescription. Desirably, the bar code corresponds to the sample code. Thus, a pharmacy employee scans the bar code with a bar code scanner 118 when a patient picks up the prescription. The pharmacy module 103 recognizes the bar code and automatically updates the management module database 112 with additional sample prescription information, such as the date and time the patent picked up the sample prescription. Alternatively, instead of using a bar code and bar code scanner, the pharmacy employee may enter a prescription identification number that corresponds to the sample code into the pharmacy module 103. This allows for the collection of data specific to the patient receipt of the sample, as adjudication through the PBM is often asynchronous to the time of pickup by a patient. A similar process integrating shipment delivery data may be used to support the collection of the data for prescriptions received at home by a patient.

It is desired that the pharmacy module 103 assist in reporting information about the sample code and the patient by interacting with a designated PBM. Typically, the PBM functions to manage eligibility, conduct utilization reviews for appropriateness of a therapy, and perform settlements between pharmacies, pharmaceutical companies and insurance companies. In this embodiment the PBM also is a primary conduit for the collection of data that is ultimately added to the USPC.

In step 209, the sample prescription information collected by the PBM is delivered back to the SPS 100 for addition to the code's file in the database 112. The PBM or the electronic prescription switch 114 may be used to analyze drug interactions between medications prescribed to patients.

In an embodiment, the pharmacy modules 103 have "keys" that enable the pharmacy module 103 to read the sample prescription submitted by the management module 104. If the pharmacy module 103 does not have the appropriate key, then the pharmacy module 103 cannot open the sample prescription. Also, the pharmacy module 103 may be given a unique pharmacy identifier. When the sample code is sent to the pharmacy module 103, the unique pharmacy identifier is automatically sent to the management module 104. If the pharmacy identifier matches pharmacy information populated in the corresponding sample code file (step 204), then the management module sends a "key" code to the pharmacy module 103 that enables the pharmacy module 103 to open the sample prescription. This is independent of verifications made on an electronic prescription by the electronic prescribing switch 114 or a PBM. Regardless of the pharmacy module's 103 ability to open a sample prescription, it is still able to adjudicate the sample with a PBM assuming the pharmacy has received an electronic prescription for the sample. The PBM receives the code information ahead of the transaction and is able to verify if the submitted transaction matches the parameters in the code. In this instance the PBM still receives all of the necessary information on the dispensing of the sample to appropriately update the sample code and files in the database 112.

Advantageously, the sample prescription need not be prepackaged in sample packets, as is commonly the case in current sample prescription allocation methods. Instead, the pharmacy may fill the sample prescription in a similar method as it would with a non-sample prescription, with an exception that the sample prescription is likely a smaller quantity of medication. Thus, the SPS process saves companies the expense of producing the sample prescription packets and also eliminates the cumbersome manual transfer by the pharmacist of media (e.g. paper vouchers or magnetic strip cards) that may represent samples and provides an automatic fully electronic process to complete the transaction. It is also contemplated that the pharmaceutical company reimburse the pharmacy for any costs incurred in filling the sample prescription, which is adjudicated electronically via a third party (e.g., a third party PBM).

In a step 210, the subscribing pharmaceutical company, having the pharmaceutical module 102, obtains sample prescription information. In general, the pharmaceutical company purchases information from the management module 104, which was acquired for the sample codes that were allotted to the pharmaceutical company in the step 200. In an embodiment, the pharmaceutical company accesses the management module web site via the pharmaceutical module 102 and navigates through the web site to a data report application. Here, the pharmaceutical company can download information stored in the database 111 after paying a fee to the management module entity. In another embodiment, the pharmaceutical company or other subscribing company is provided with a unique identification number, after paying a fee, that allows them to access the sample code files. Preferably, the pharmaceutical company has access limited to only non-confidential information. For example, the pharmaceutical company may be denied access to private patient information, such as social security numbers or names, but has access to non-confidential information such as demographic and metric data. Thus, the pharmaceutical company has access to valuable marketing information, but yet does not violate a patient's confidentiality rights.

Figure 3:
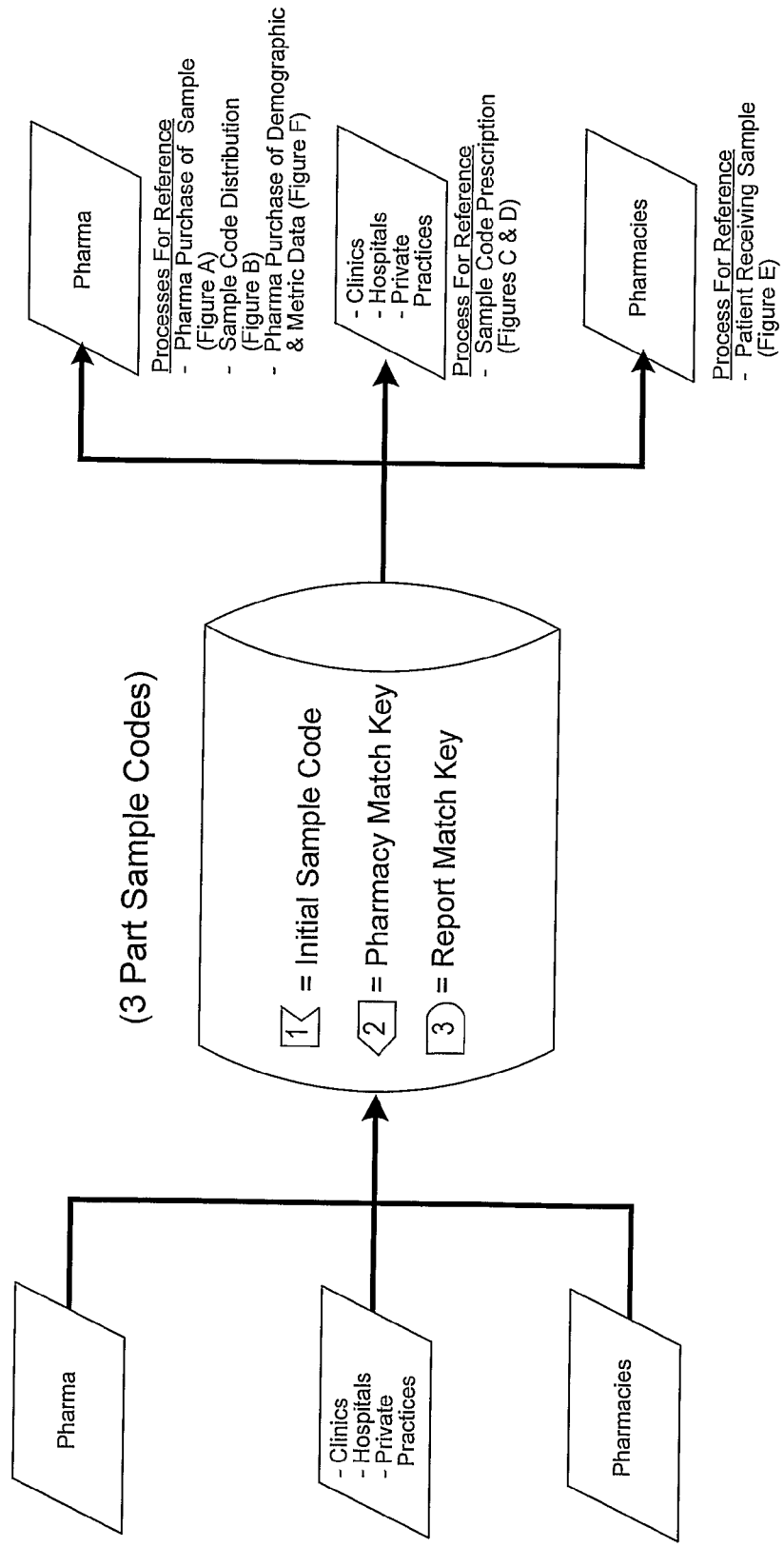
FIG. 3 is a diagrammatic illustration of an embodiment of a sample code and illustrates a flow of information among components of the present invention.

Although the present invention has been described in considerable detail with reference to certain preferred embodiments thereof, other versions are possible. For example, one embodiment uses the codes shown in FIG. 3 and a further embodiment uses the sample prescription system process shown in FIG. 4 A-F. Also, many of the steps described herein may be accomplished via mail, fax or other communication method instead of the Internet. Additionally, it is contemplated that the embodiments of the present invention can be used with regular prescriptions as well as sample prescriptions.

Therefore, the spirit and scope of the invention should not be limited to the description of the preferred embodiments contained herein.

I claim:

1. A method of managing and tracking sample pharmaceutical products performed by a computing device, the method comprising:
   creating a tracking code and a corresponding electronic prescription data file in response to an electronic activation of tracking code allotments by a pharmaceutical company, wherein the pharmaceutical company accesses a computer operated management module of a sample prescription system through a computer operated pharmaceutical module via an Internet connection;
   assigning pharmaceutical product information to the electronic prescription data file which corresponds to the tracking code obtained by the pharmaceutical company through access of the management module;
   storing the tracking code and the electronic prescription data file in a database of the management module;
   electronically distributing the tracking code for the assigned pharmaceutical product to a prescriber from the pharmaceutical company;
   confirming tracking code allotments for the assigned pharmaceutical by the prescriber, wherein the prescriber accesses the management module of the sample prescription system through a computer operated prescriber module via an Internet connection;
   electronically adding prescription information regarding a patient into the electronic prescription data file by the prescriber through communication with the management module through the prescriber module;
   electronically sending the tracking code and the corresponding electronic prescription data file containing the prescription information to the management module;
   electronically sending the tracking code and the corresponding electronic prescription data file containing the prescription information from the management module to a pharmacy through an eRx switch, wherein the pharmacy is a separate entity than the prescriber; and electronically populating the electronic prescription data file with prescription tracking information by the pharmacy, wherein the pharmacy accesses the management module through the pharmacy module via an Internet connection.

2. The method of claim 1, wherein the tracking code and the electronic prescription data file comprises an encrypted character string and the method further comprises:

adding new content to the electronic prescription data file; and encrypting the new content into the encrypted character string.

3. The method of claim 2, wherein the steps of adding new content and encrypting the new content are performed several times during a life-cycle of the sample pharmaceutical product.

4. The method of claim 2, wherein the new content comprises at least one of prescriber information, patient information, dispensing location information, tracking information and prescription information.

5. The method of claim 1, further comprising requesting the generation of the electronic prescription data file by the pharmaceutical company.

6. The method of claim 1, further comprising transmitting the tracking code to a subscriber.

7. The method of claim 1, wherein the sample pharmaceutical product information comprises at least one of a sample prescription medication type, terms of the sample pharmaceutical product, and a length of time during which tracking code and the electronic prescription data file is valid.

8. The method of claim 1, further comprising verifying the tracking code is valid and that the prescription originated from the management module prior to dispensing the pharmaceutical product by the pharmacy through communication with a pharmacy benefit manager by use of the pharmacy module.

* * * * *